(12) United States Patent
Tin et al.

(10) Patent No.: US 9,134,121 B2
(45) Date of Patent: Sep. 15, 2015

(54) DETERMINING MATERIAL PROPERTIES USING SPECKLE STATISTICS

(75) Inventors: Siu-Kei Tin, Milpitas, CA (US); Francisco Imai, Mountain View, CA (US)

(73) Assignee: CANON KABUSHIKI KAISHA, Tokyo (JP)

( * ) Notice: Subject to any disclaimer, the term of this patent is extended or adjusted under 35 U.S.C. 154(b) by 330 days.

(21) Appl. No.: 13/589,577

(22) Filed: Aug. 20, 2012

(65) Prior Publication Data

US 2014/0049779 A1 Feb. 20, 2014

(51) Int. Cl.
*G01B 11/30* (2006.01)
*G01B 9/02* (2006.01)
*G01N 21/47* (2006.01)

(52) U.S. Cl.
CPC ............. *G01B 11/30* (2013.01); *G01B 11/303* (2013.01); *G01N 21/474* (2013.01); *G01B 9/02094* (2013.01); *G01N 2021/479* (2013.01)

(58) Field of Classification Search
CPC .. G01B 11/30; G01B 11/303; G01B 9/02094; G01B 9/02095; G01B 9/02096; G01J 3/45; G01N 2021/479
USPC .................. 356/35.5, 450–521, 600
See application file for complete search history.

(56) References Cited

U.S. PATENT DOCUMENTS 4,145,140 A * 3/1979 Fujii ............................. 356/512
8,058,617 B2 11/2011 Vincent et al.
2008/0123106 A1 * 5/2008 Zeng et al. ................... 356/600
2008/0154524 A1 6/2008 Shirley
2008/0158550 A1 7/2008 Arieli et al. ..................... 356/73
2010/0014141 A1 * 1/2010 Lapchuk et al. ............ 359/204.2
2011/0013002 A1 * 1/2011 Thompson et al. ............. 348/77
2011/0235871 A1 * 9/2011 Byren et al. .................. 382/124
2011/0242285 A1 10/2011 Byren ............................. 348/47
2011/0268312 A1 * 11/2011 Imaizumi ...................... 382/100

OTHER PUBLICATIONS

International Search Report and Written Opinion dated Nov. 22, 2013 in counterpart PCT/US2013/054962.
Le, et al., "Semiconductor Laser Multi-Spectral Sensing and Imaging", Sensors 2010, Jan. 13, 2010.
Borkowski et al., "Sensitivity of a 'dispersed-speckles' piston sensor for multi-aperture interferometers and hypertelescopes", Astronomy and Astrophysics, Sep. 9, 2004.
Shirley et al., "Nonconventional 3D Imaging Using Wavelength-Dependent Speckle", MIT Lincoln Laboratory Journal, vol. 9, No. 2, pp. 153-186, 1996.
http://brownengineering.blogspot.com/2012/04/single-nanomaterial-yields-many-laser.html, Apr. 30, 2012.

(Continued)

*Primary Examiner* — Tarifur Chowdhury
*Assistant Examiner* — Michael P Lapage
(74) *Attorney, Agent, or Firm* — Fitzpatrick, Cella, Harper & Scinto

(57) ABSTRACT

A property of a material is determined. The material is illuminated with a light beam of controlled spectral and coherence properties. A stack of speckle field images is recorded from speckle fields reflected from the illuminated material in multiple spectral channels. The stack of speckle field images includes multiple speckle field images each being recorded in a respectively different spectral channel. Statistical properties of the speckle field images in the stack of speckle field images are analyzed to determine at least one property of the illuminated material.

15 Claims, 6 Drawing Sheets

(56) References Cited

OTHER PUBLICATIONS http://www.foveon.com/article.php?a=67, 2010.
http://www.imaging.org/ist/publications/reporter/articles/REP27_1_CIC19_LIN_PG332.pdf, 2011.

International Preliminary Report on Patentability dated Feb. 24, 2015, issued in corresponding PCT Application No. PCT/US2013/054962.

* cited by examiner

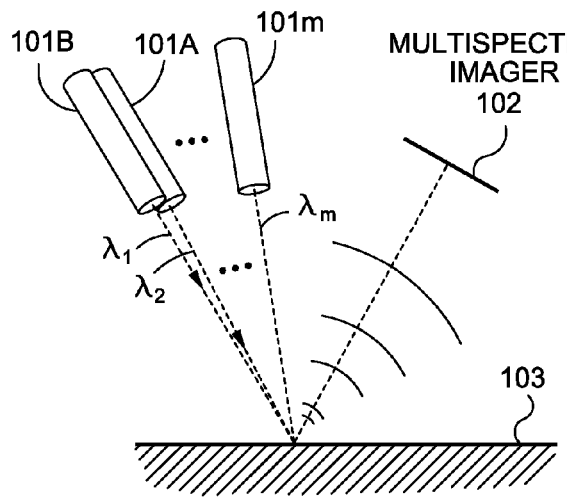
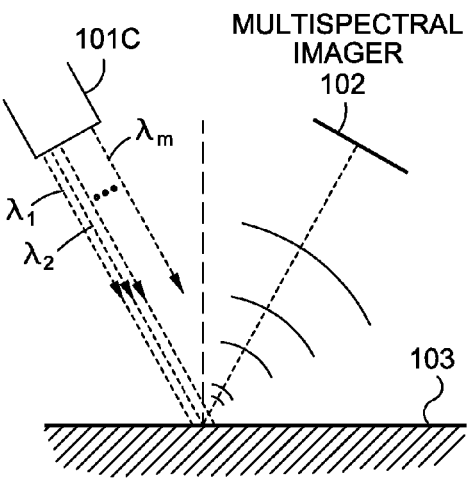
FIG. 1A
FIG. 1B
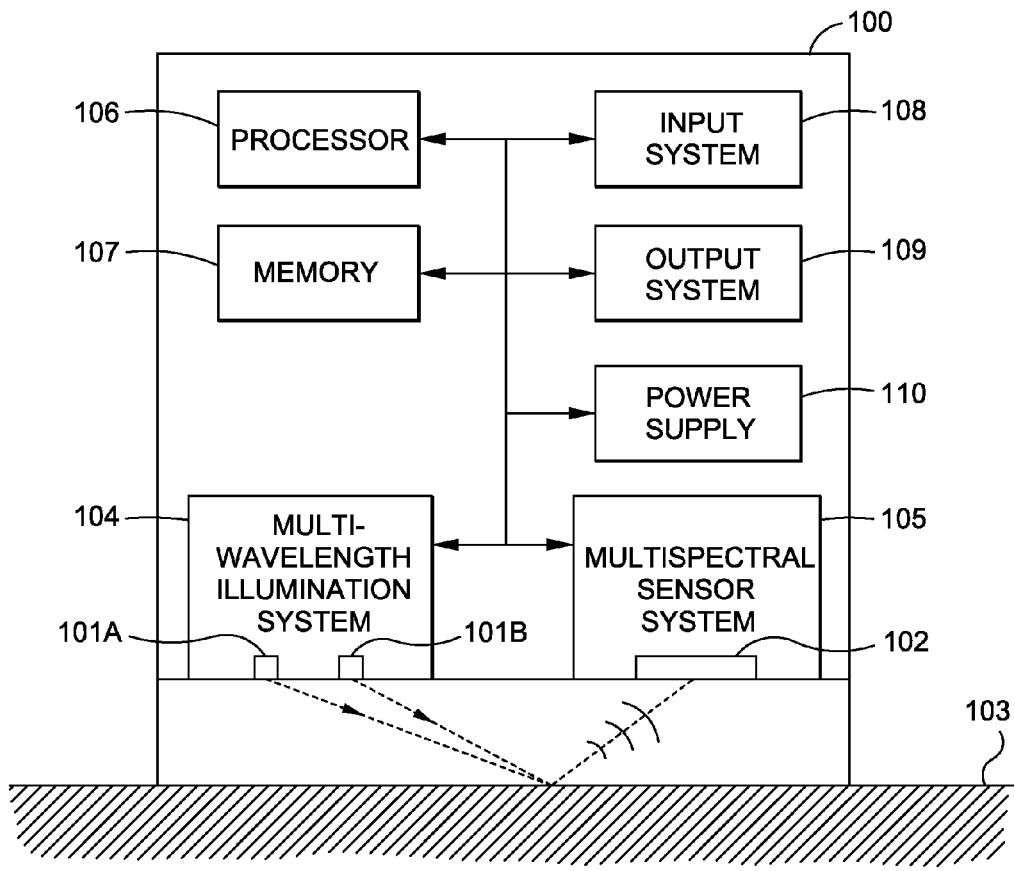
FIG. 1C

DETERMINING MATERIAL PROPERTIES USING SPECKLE STATISTICS

FIELD

The present disclosure relates to determining properties of a material, and more particularly relates to determining properties of a material based in part on speckle statistics.

BACKGROUND

One area of research beneficial to machine automation concerns automatic determination of a material, such as determination of the properties of the material or identification and/or discrimination of the material, particularly without contact to the material. For example, in robotic assembly or sorting plants, it can be important to identify objects or parts by optical means based on their material properties for assembling or sorting purposes.

In this context, it has been considered to measure statistics of a speckle pattern, to assist in a non-contact estimation of properties of a material or identification thereof. A speckle pattern results from interference of light waves scattered by a material when illuminated by a light source (such as a laser) with controlled coherence properties.

SUMMARY

There have been attempts to correlate speckle statistics with surface roughness. Nevertheless, attempts to correlate speckle statistics with surface roughness have generally been unsatisfactory. In particular, conventional attempts use a monochromatic coherent light source such as a laser. The detectable surface roughness is limited to being of the same order of magnitude as the wavelength of the laser. In other words, the range of surface roughness to be measured needs to be known in advance so that a laser of suitable wavelength can be chosen. In some applications, the range of surface roughness to be measured may be known in advance. In general, however, the range of surface roughness to be measured may be unknown, or multiple materials involving multiple ranges of surface roughness may be of interest.

In addition, in the field of material identification and discrimination, surface roughness is only one of the material properties that may be used to identify and discriminate materials.

The foregoing situation is addressed by analyzing statistical properties of speckle field images in a stack of speckle field images, each of the images in the stack being recorded in a respectively different spectral channel.

Thus, in an example embodiment in which a property of a material is determined, the material is illuminated with a light beam of controlled spectral and coherence properties. A stack of speckle field images is recorded from speckle fields reflected from the illuminated material in multiple spectral channels. The stack of speckle field images includes multiple speckle field images each being recorded in a respectively different spectral channel. Statistical properties of the speckle field images in the stack of speckle field images are analyzed to determine at least one property of the illuminated material.

By analyzing statistical properties of speckle field images in a stack of speckle field images, it is ordinarily possible to estimate surface roughness without prior knowledge of the range of surface roughness of the materials being measured.

In further aspects of some representative embodiments, a feature vector is formed based on the analysis of statistical properties of the speckle field images in the stack of speckle field images, and the feature vector is compared to a database of such feature vectors. Each entry in the database comprises a feature vector matched to an identification of a material from which the feature vector is derived. An identity of the illuminated material is derived based on the comparison.

In other aspects, the stack of speckle field images is captured simultaneously using, for example, a multispectral image sensor, or the stack is captured sequentially using a monochrome image sensor.

In still other aspects of some representative embodiments, the light beam of controlled spectral and coherence properties includes one or more light sources which together illuminate the material with multiple wavelengths. The analysis of statistical properties of the speckle field images in the stack of speckle field images includes estimating a monochromatic speckle field for each of the multiple wavelengths from the stack of speckle field images. The one or more light sources are applied simultaneously or sequentially.

In yet another aspect, the analysis of statistical properties of the speckle field images in the stack of speckle field images further includes computation of a monochromatic speckle contrast for each monochromatic speckle field.

In another aspect, the analysis includes combining multiple monochromatic speckle fields to form multiple new speckle fields, each new speckle field having a respectively different coherence length, deriving a polychromatic speckle contrast from each of the new speckle fields, and estimating surface roughness of the illuminated material by using the polychromatic speckle contrasts corresponding to coherent lengths that are commensurate with the surface roughness.

In still another aspect, the analysis includes computing a correlation matrix from the monochromatic speckle fields, where dimensionality of the correlation matrix is based on the number of wavelengths, and estimating surface roughness of the illuminated material from the correlation matrix.

In another aspect, the analysis includes calculating one or more speckle statistics from each of the monochromatic speckle fields, deriving a feature vector by pooling all of the calculated speckle statistics, and determining a property of the illuminated material from the feature vector.

This brief summary has been provided so that the nature of this disclosure may be understood quickly. A more complete understanding can be obtained by reference to the following detailed description and to the attached drawings.

BRIEF DESCRIPTION OF THE DRAWINGS

FIGS. 1A to 1H are views for explaining a material property determination device according to example embodiments.

DETAILED DESCRIPTION

Figure 1D:
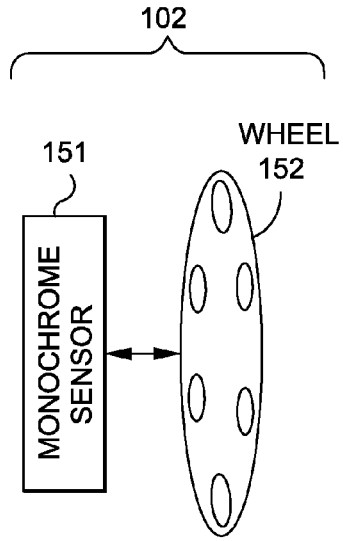

FIGS. 1A to 1C are views for explaining a material identification device for identifying a material using a stack of speckle field images.

In particular, FIGS. 1A to 1C are views for explaining a device which illuminates a material with a light beam of controlled spectral and coherence properties. A stack of speckle field images is recorded from speckle fields reflected from the illuminated material in multiple spectral channels.

In the simplified view shown in FIG. 1A, light sources 101A and 101B illuminate a material 103 with light beams with controlled coherence properties and different wavelengths. Light sources 101A and 101B are elements which emit a light beam with controlled coherence properties. For example, light sources 101A and 101B might each comprise a monochromatic laser beam. In some embodiments, light sources 101A and 101B each include a laser light source. Thus, a light source according to the disclosure might comprise multiple coherent light sources each comprised of a laser with a respectively different wavelength, as shown in FIG. 1A. In such a case, the multiple different light sources may be applied simultaneously or sequentially.

Meanwhile, FIG. 1B shows another example embodiment, in which a single light source 101C is a spatially coherent light source with multiple wavelengths, e.g., a polychromatic laser.

As shown in FIGS. 1A and 1B, the material 103 is illuminated with m multiple wavelengths. The number of wavelengths m can be large or small depending on resources and/or capabilities.

In that regard, it should be understood that any number or variety of light sources could be used in various embodiments. Multiple wavelengths may be obtained using multiple lasing materials and/or lasing modes. For example, the laser may be based on a semiconductor such as aluminum gallium indium phosphide (AlGaInP). Alternative lasing materials including gases such as helium-neon (HeNe) may be used. Multiple wavelengths may also be achieved using a single material such as a dye. Other examples include a liquid crystal laser, and a laser based on a nanomaterial.

Multispectral imager 102 is positioned at a designated observation point to record the speckle pattern in multiple spectral channels, resulting in a speckle field stack. Multispectral imager 102 may be based on one or more CMOS or CCD sensors and multiple color filters with different spectral passbands. The color filters may form a color filter array or mosaic in the case of a single sensor, or each color filter may be associated with a sensor in the case of multiple sensors. Alternatively, instead of color filters, a layered sensor stack design may be used. Yet another alternative is a sensor with tunable spectral sensitivities. Multispectral imager 102 may also comprise a monochrome sensor which captures a stack of spectral images sequentially. Example embodiments of multispectral imager 102 will be described more fully below with respect to FIGS. 1D to 1H.

In addition to the free space geometry suggested in FIGS. 1A and 1B, other imaging geometry may be used. For example, multispectral imager 102 may include additional focusing optics between the scene and the sensor, such as an imaging lens.

Material 103 may comprise, for example, a translucent material such as skin tissue, or a material to be sorted such as a recyclable material.

FIG. 1C is a view of a material property determination device 100 for determining a property of the material 103 as shown in FIGS. 1A and 1B. In that regard, material property determination device 100 is shown in FIG. 1C as a device which is placed on or near to material 103, but it should be understood that material property determination device 100 might be embodied in other arrangements and with other positioning relative to material 103. For example, material property determination device 100 could be arranged in other housings or devices which include a light source and multispectral imager as shown in FIGS. 1A and 1B. In addition, the elements of FIGS. 1A to 1C could be embodied in separate devices or across multiple separate devices in a system, at different locations. For example, laser beams 101A and 101B and multispectral imager 102 could be embodied in two or more devices.

As shown in FIG. 1C, material property determination device 100 includes light sources 101A and 101B (i.e., according to the example embodiment of FIG. 1A), multispectral imager 102, multi-wavelength illumination system 104, multi-spectral sensor system 105, processor 106, memory 107, input system 108, output system 109 and power supply 110. Of course, material property determination device 100 could include a single light source 101C with multiple wavelengths (as shown in FIG. 1B) instead of multiple light sources 101A and 101B.

Light sources 101A and 101B illuminate a material 103 with light beams with controlled coherence properties and different wavelengths, and multispectral imager 102 records the speckle field images in multiple spectral channels.

In that regard, speckle patterns are formed when a material is illuminated by a coherent light such as a laser. A pattern is observed from the scattering of the coherent light caused in part by the surface microstructure of the illuminated material. When a speckle pattern is recorded on a sensor, it is called a speckle field image. The speckle pattern has statistical properties can be correlated to the material properties of illuminated material. In one example described herein, the determined property is a surface roughness.

The light used for the illumination should have controlled coherence properties, because the speckle pattern is caused by the interference of coherent light waves reflected from the material. Ordinarily, coherence may refer to spatial coherence (e.g., light waves remaining correlated over a long distance, possibly averaged over time) and temporal coherence (e.g., light waves remaining correlated over long time). One example of a light source with spatial and temporal coherence is a monochromatic laser.

Multi-wavelength illumination system 104 is a system for driving light source(s) 101A and/or 101B to illuminate material 103 with multiple wavelengths. In that regard, multi-wavelength illumination system 104 might comprise, for example, one or more parts for controlling light source(s) 101A and/or 101B to operate simultaneously or sequentially.

Multispectral sensor system 105 is a system for recording multiple speckle field images from speckle fields reflected from material 103 illuminated by light source(s) 101A and/or 101B with different wavelengths. Multispectral sensor system 105 might comprise parts for controlling multispectral imager 102 so as to sense the speckle patterns resulting from illumination from light sources with different wavelengths, or might comprise a selection system of multiple imaging devices with different filters that constitute the multispectral imager 102, set so as to record the speckle field images caused by different wavelengths.

Processor 106 is a computer processor such as a single core or multi-core central processing unit (CPU) or micro-processing unit (MPU), which is constructed to realize functionality according to the disclosure. Processor 106 might comprise multiple computer processors which are constructed to work together. Processor 106 communicates with the elements of identification device 100 to control the elements to perform required functionality or to obtain required data. For example, processor 106 may control multi-wavelength illumination system 104 to illuminate material 103 with light of multiple wavelengths, and may control multispectral sensor system 105 to drive multispectral imager 102 to record speckle field images in multiple spectral channels.

Memory 107 stores constants, computer-executable programs, and the like for operation of processor 106, including programs for execution of various flowcharts. Memory 107 may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like.

Figure 3:
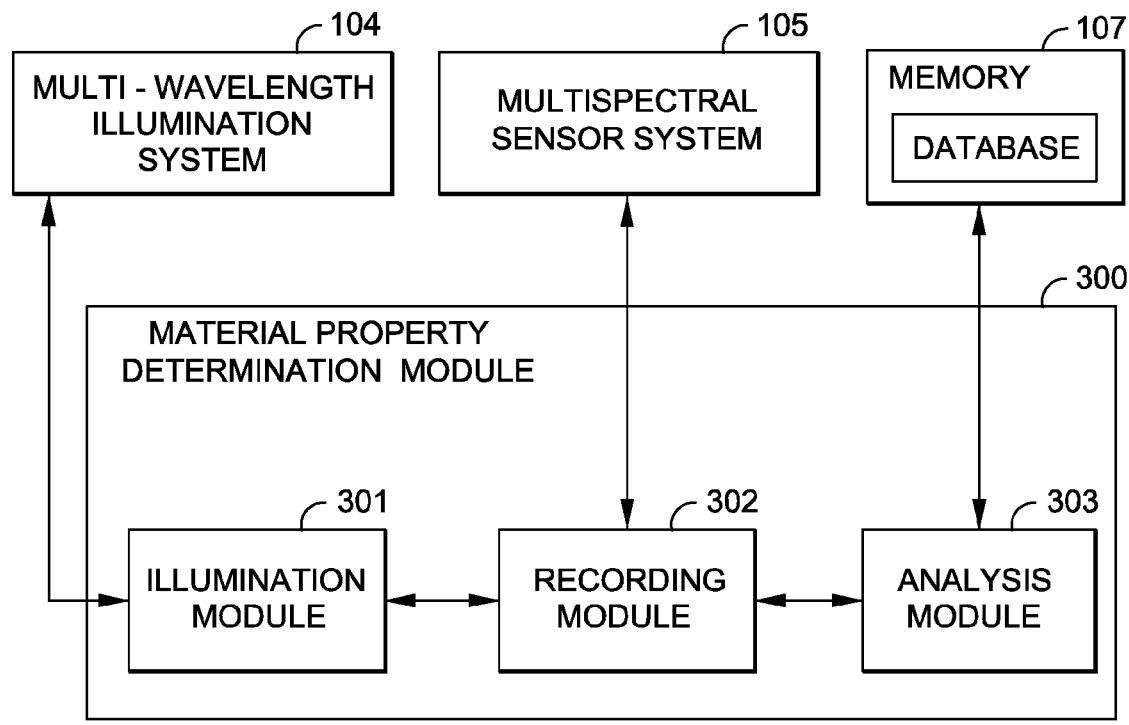
FIG. 3 is a simplified block diagram for explaining a material property determination module according to an example embodiment.

Memory 107 may retrievably store thereon material property determination module 300 as described herein and shown in FIG. 3. According to this example embodiment, the material property determination module 300 includes at least an illumination module 301 for illuminating the material with a light beam of controlled spectral and coherence properties, and a recording module 302 for recording a stack of speckle field images from speckle fields reflected from the illuminated material in multiple spectral channels. The stack of speckle field images includes multiple speckle field images each being recorded in a respectively different spectral channel. The material property determination module 300 further includes an analysis module 303 for analyzing statistical properties of the speckle field images in the stack of speckle field images to determine at least one property of the illuminated material.

Input system 108 inputs data such as settings or control parameters for operation of material property determination device 100. For example, in some example embodiments, it might be useful to input precise control parameters from an external processing device such as a computer. Accordingly, input system 108 may include a connection and associated elements for communicating with other devices.

Output system 109 provides output of data obtained or produced from material property determination device 100, either to a user, e.g., via a display in output system 109 or via a connection to output data to an external device.

Power supply 110 is a primary power source such as an alkaline battery or a lithium battery, a secondary battery such as a NiCd battery, a NiMH battery or a Li battery, or the like for providing power to material property determination device 100.

In FIG. 1C, material property determination device 100 is shown as a standalone device, but other embodiments might involve multi-wavelength illumination system 104 and/or multispectral sensor system 105 in a first housing coupled to remaining components in a second housing, such as by unshown wireless or wired interfaces to a computer.

FIGS. 1D to 1H are views for explaining a spectral imaging system in multispectral imager 102 for capturing spectral information according to example embodiments. These embodiments are shown merely for purposes of example, and other arrangements are possible. For example, in some embodiments an image sensor 14 may be constructed to capture high-resolution additional spectral data itself, and thus additional hardware may not be necessary.

Figure 1E:
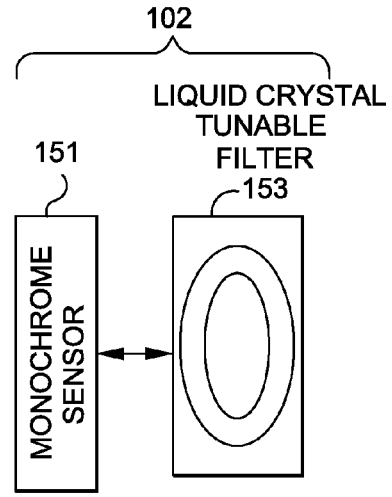

FIGS. 1D and 1E depict embodiments with a monochrome sensor 151 and a set of narrow-band filters. The narrow-band filters, in turn, can be comprised of a filter wheel 152 (FIG. 1D) with filters with different spectral bands, or a liquid crystal tunable filter 153 (FIG. 1E). Either of these embodiments ordinarily provides relatively high spectral resolution and relatively high spatial resolution. However, due to cost and size of the system, such embodiments ordinarily are only appropriate for high-end imaging of static materials, taking into account the imaging capture time needed to move the filter wheel or to capture images using the liquid crystal tunable filter.

Figure 1F:
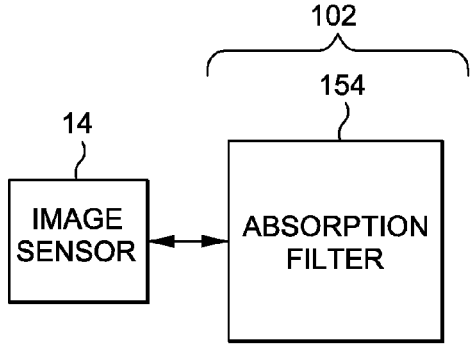

FIG. 1F depicts an embodiment in which image sensor 14 is an RGB sensor combined with an absorption filter 154, for example as shown in U.S. Pat. No. 7,554,586, "System and method for scene image acquisition and spectral estimation using a wide-band multi-channel image capture", the contents of which are incorporated by reference herein. The captured RGB from image sensor 14 without an external filter provides the traditional image capture. Meanwhile, a spectral reflectance estimation process is performed to get higher spectral resolution data from lower spectral resolution captured data provided by the combination of unfiltered images from image sensor 14, and filtered RGB images from absorption filter 154. The external absorption filter 154 changes the overall sensitivities of the original RGB sensor providing three additional channels. This embodiment provides relatively high spatial resolution and is relatively usable for dynamic scenes if the filter 154 is fast-switching, and there is ordinarily no need for a secondary sensor as in the embodiments of FIGS. 1D and 1E. On the other hand, the embodiment of FIG. 1F tends to have relatively low spectral resolution.

Figure 1G:
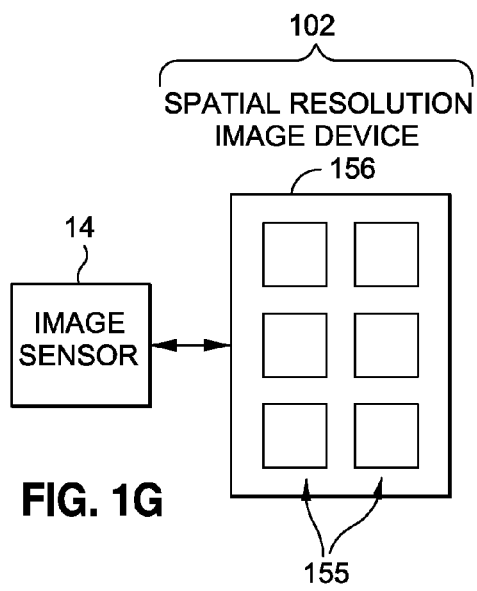

FIG. 1G depicts an embodiment in which image sensor 14 is an RGB sensor combined with an additional high-spectral resolution but low-spatial resolution imaging device 156, for example a device which includes an array of spectral sensing devices 155 with high-spectral resolution such as an array of filters with distinct spectral transmittances, such as described in U.S. Publications Nos. 2010/0045050, 2010/0046077, 2010/0053755 and 2010/0182598, the contents of which are incorporated by reference herein. Main RGB imaging sensor 14 provides the conventional photography capture, whereas a secondary sensor (array of high-spectral resolution sensors) 155 works as a low-spatial resolution but high-spectral resolution spectral measurement device. The arrangement of FIG. 1G provides high spectral resolution with relatively low cost, and can be applied to dynamic scenes. On the other hand, due to the relatively low resolution of the secondary stage (e.g., the array of spectral sensing devices), this configuration ordinarily has a low spatial resolution.

Figure 1H:
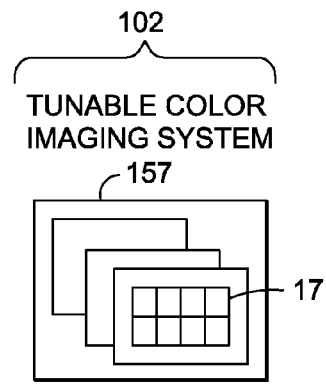

FIG. 1H depicts an example embodiment in which image sensor 14 is a color imaging system 157 with tunable spectral sensitivities. The tunable spectral sensitivities may be tunable in accordance with a capture parameter 17. This arrangement is described in detail in U.S. application Ser. No. 12/949,592, by Francisco Imai, entitled "Adaptive Spectral Imaging By Using An Imaging Assembly With Tunable Spectral Sensitivities", the contents of which are incorporated by reference herein.

As mentioned above, image sensor 14 may itself have high spectral resolution and capture additional multi-spectral data. Thus, additional hardware might not be necessary at all, although multiple captures might be needed.

Figure 2:
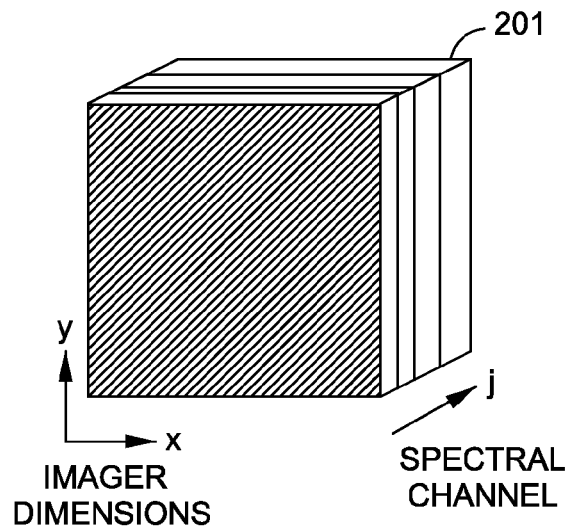
FIG. 2 is a view for explaining a stack of speckle field images according to an example embodiment.

FIG. 2 is a view for explaining a stack of speckle field images, each in a different spectral channel. Thus, as can be seen from FIG. 2, the stack is comprised of multiple speckle field images in different spectral channels based on the imager dimensions. In this regard, it should be understood that FIG. 2 is simply for purposes of explanation, and that the speckle field images do not necessarily need to be stored together. Moreover, a respective speckle field is ordinarily not obtained for every wavelength, but rather for each spectral channel. Spectral channel, in this case, refers to the channels captured by the capturing device (e.g., multispectral imager 102) which generally encompass multiple wavelengths. Additionally, the disclosure is not limited to visible light, nor is it limited to RGB channels.

FIG. 3 is a simplified block diagram for explaining a material property determination module according to an example embodiment. Material property identification module 300 comprises computer-executable process steps stored on a non-transitory computer-readable storage medium, such as memory 107. More or less modules may be used, and other architectures are possible.

As shown in FIG. 3, material property determination module 300 includes at least an illumination module 301 for illuminating the material with a light beam of controlled spectral and coherence properties. To that end, illumination module 301 communicates with multi-wavelength illumination system 104. Material property determination module 300 further includes recording module 302 for recording a stack of speckle field images from speckle fields reflected from the illuminated material in multiple spectral channels. To that end, recording module 302 communicates with multispectral sensor system 105. The stack of speckle field images includes multiple speckle field images each being recorded in a respectively different spectral channel. The material property determination module 300 further includes an analysis module 303 for analyzing statistical properties of the speckle field images in the stack of speckle field images to determine at least one property of the illuminated material. In another embodiment, analysis module 303 further forms a feature vector based on the analysis of statistical properties of the speckle field images in the stack of speckle field images, compares the feature vector to a database of such feature vectors, where each entry in the database comprises a feature vector matched to an identification of a material from which the feature vector is derived, and derive an identity of the illuminated material based on the comparison. Thus, analysis module 303 communicates with a database which, in the example shown in FIG. 3, is stored in memory 107. The database may store, for example, feature vectors matched to respective identifications of materials from which the feature vectors are derived. For example, a feature vector consisting of feature values may be used for identifying and discriminating materials. The feature values can be derived from measurements, such as measurements using a light source with multiple wavelengths or otherwise controlled spectral properties.

Figure 4A:
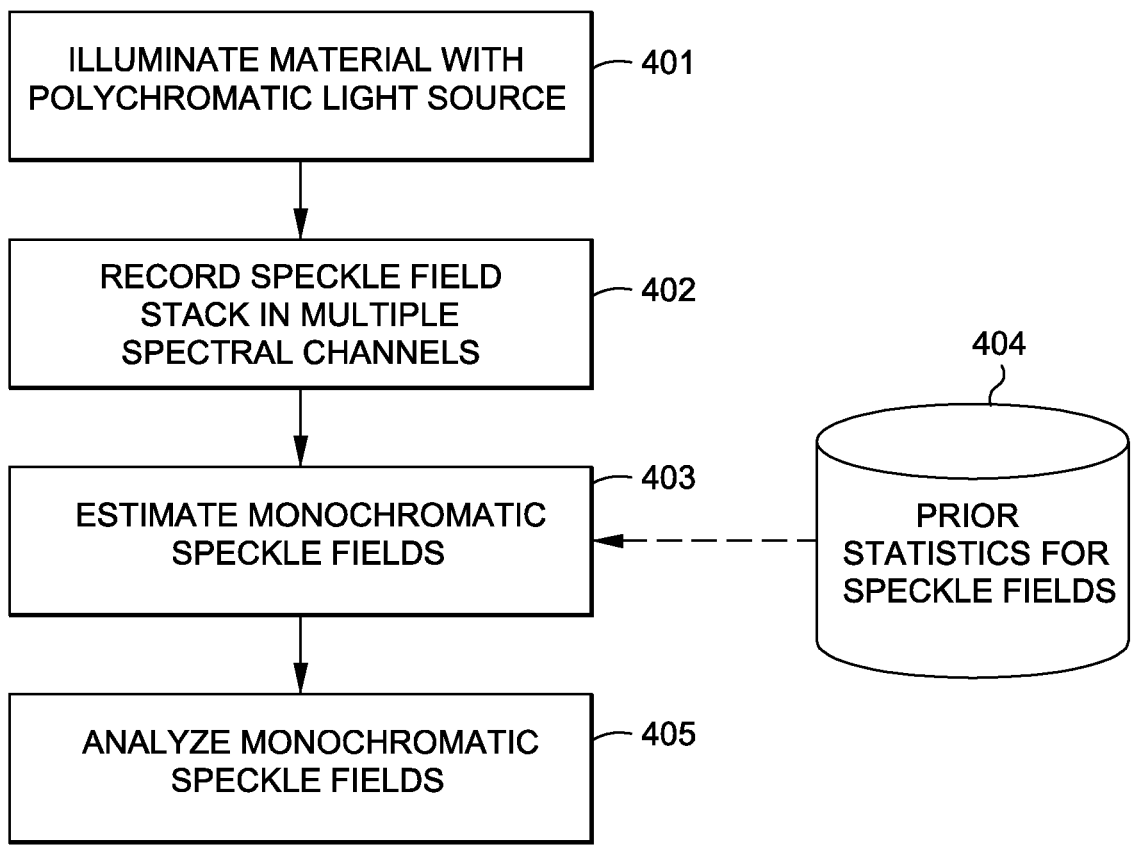
FIGS. 4A and 4B are flow diagrams for explaining processing in the device shown in FIGS. 1A and 1B according to an example embodiment.
Figure 4B:
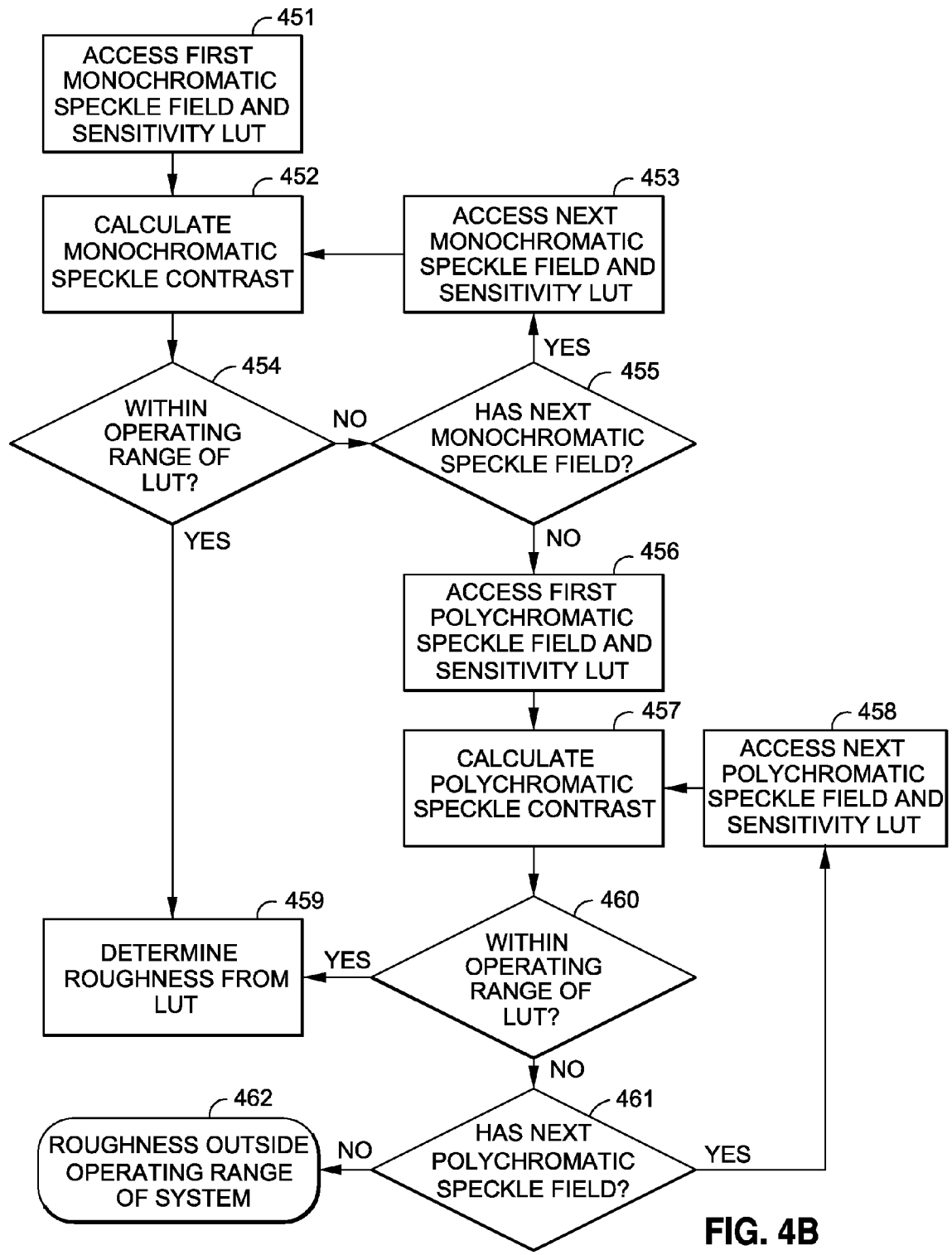

FIGS. 4A and 4B are flow diagrams for explaining processing in the device shown in FIG. 1C according to an example embodiment.

Briefly, in FIG. 4A, a property of a material is determined. The material is illuminated with a light beam of controlled spectral and coherence properties. A stack of speckle field images is recorded from speckle fields reflected from the illuminated material in multiple spectral channels. The stack of speckle field images includes multiple speckle field images each being recorded in a respectively different spectral channel. Statistical properties of the speckle field images in the stack of speckle field images are analyzed to determine at least one property of the illuminated material.

In more detail, in step 401, the material is illuminated with a polychromatic light source. In this regard, the polychromatic light source might comprise multiple light sources such as light sources 101A and 101B shown in FIG. 1A, or might comprise a single, spatially coherent light source with multiple wavelengths, e.g., a single polychromatic laser as shown in FIG. 1B.

For a polychromatic light source consisting of wavelengths $\lambda_1, \lambda_2, \ldots, \lambda_m$, if each wavelength could be isolated and each acted individually, and the m speckle patterns were recorded separately with a panchromatic imager having unit sensitivity, then the individual monochromatic speckle (intensity) fields would be $A_1(x, y), A_2(x, y), \ldots, A_m(x, y)$.

A monochrome imager is conventionally used to record a speckle field image. If a monochrome imager with spectral sensitivity $s(\lambda)$ is used, then the recorded speckle field image is:

$$K(x, y) = \sum_{i=1}^{m} s(\lambda_i) A_i(x, y) \tag{1}$$

In other words, with a conventional monochrome imager, only $K(x, y)$ can be recorded directly but not $A_1(x, y), A_2(x, y), \ldots, A_m(x, y)$. Thus, conventionally, it is not possible to determine or reliably estimate all the monochromatic speckle fields $A_1(x, y), A_2(x, y), \ldots, A_m(x, y)$ from one speckle field $K(x, y)$.

Accordingly, in step 402, a stack of speckle field images is recorded from speckle fields reflected from the illuminated material in multiple spectral channels. In that regard, if a multispectral imager with n spectral channels and corresponding spectral sensitivities $s_1(\lambda), s_2(\lambda), \ldots, s_n(\lambda)$ is used (such as multispectral imager 102), then the speckle field stack is composed of n speckle field images, given by $$K_j(x, y) = \sum_{i=1}^{m} s_j(\lambda_i) A_i(x, y). \tag{2}$$

where $j = 1, 2, \ldots, n$

Based on the above stack of speckle field images in multiple spectral channels, the monochromatic speckle fields are estimated in step 403. In some examples, estimating a monochromatic speckle field for each of the multiple wavelengths comprises solving an inverse problem based on spectral sensitivities of the multiple spectral channels.

In an embodiment, the condition n m is satisfied, and it becomes possible to determine or reliably estimate the monochromatic speckle fields $A_1(x, y), A_2(x, y), \ldots, A_m(x, y)$. In particular, in this case, there are at least as many spectral channels as wavelengths, and the monochromatic speckle fields are estimated by a best fit solution. For example, for each pixel location (x, y), equation (2) provides an overdetermined set of linear equations in the $A_i$'s. This can be solved by a best fit solution that has least squares error in the spectral channels. This is generally equivalent to finding the Moore-Penrose pseudoinverse. Alternatively, the solution can also be obtained by numerical computation methods such as singular value decomposition (SVD).

In another embodiment, the condition n<m is satisfied, equation (2) is underdetermined, and there is no unique solution. The monochromatic speckle fields $A_1(x, y), A_2(x, y), \ldots, A_m(x, y)$ can be estimated by assuming additional regularizing constraints, wherein a prior is assumed on the statistical distribution of spectra of speckle fields. The estimation of monochromatic speckle fields may access prior statistics for speckle fields 404, which may be stored, for example, in memory 107.

For example, the monochromatic speckle fields can be estimated by the solution with least squares error for the wavelengths, i.e., spectral RMS error. This can be achieved for instance by the Weiner estimation method. The covariance matrix (which is prior statistics of the spectra of speckle fields) needed in the Weiner estimation may be predetermined by a calibration process wherein the speckle fields are measured using a hyperspectral camera. Alternatively, instead of a hyperspectral camera, multiple locations of the speckle fields may be measured using a spectroradiometer. This covariance matrix can then be included in prior statistics for speckle fields 404, which may be stored in memory 107. The prior statistics in turn provide a regularizing constraint (penalty term) for solving the undetermined (ill-posed) inverse problem. Thus, in this case, there are fewer spectral channels than wavelengths, and the monochromatic speckle fields are estimated by solving an underdetermined inverse problem with additional regularizing constraints.

Once $A_1(x, y), A_2(x, y), \ldots, A_m(x, y)$ are determined, they can be used in further analysis.

Thus, in step 405, the monochromatic speckle fields are analyzed. This analysis can be performed in a number of ways. In one example, the analysis can be incorporated into the program logic of a speckle-based optical profilometer (e.g., material property determination device 100) that is adaptive to a wide range of surface roughness.

In this regard, analysis of statistical properties of the speckle field images in the stack of speckle field images can include computation of a monochromatic speckle contrast for each monochromatic speckle field. Generally, a speckle contrast can be computed from a speckle field image. In particular, given any speckle field A, a speckle contrast C for the speckle field A is computed as $C=\sigma_A/\mu_A$, where $\sigma_A$ is the standard deviation of A and $\mu_A$ is the mean of A. A monochromatic speckle contrast refers to a speckle contrast arising from a monochromatic speckle field. Similarly, a polychromatic speckle contrast refers to a speckle contrast arising from a polychromatic speckle field.

For example, each monochromatic speckle field $A_i(x, y)$ can be used in the computation of monochromatic speckle contrast, suitable for estimating surface roughness of the order of approximately $0.4\lambda_i$. Even if the light source is a "monochromatic" laser, it may have a finite spectral width, so that the speckle contrast from a direct measurement using a monochrome imager may have a lower contrast than predicted due to the finite spectral width.

Thus, in this example, the light beam of controlled spectral and coherence properties includes one or more light sources which together illuminate the material with multiple wavelengths. The analysis of statistical properties of the speckle field images in the stack of speckle field images includes estimating a monochromatic speckle field for each of the multiple wavelengths from the stack of speckle field images. The one or more light sources are applied simultaneously or sequentially.

Figure 5:
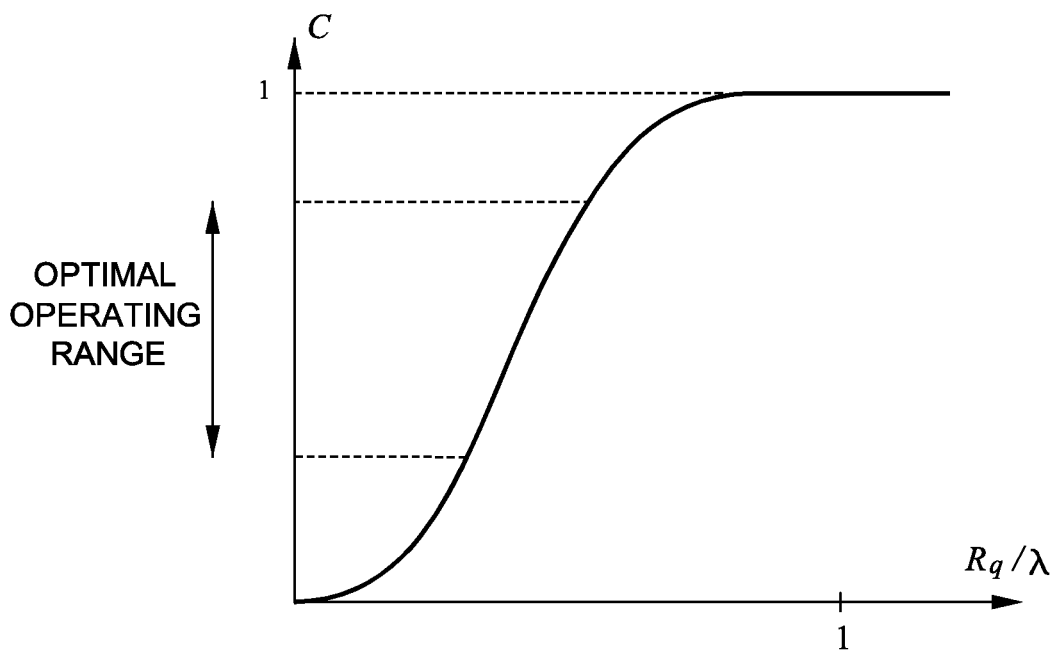
FIG. 5 is a view for explaining a relationship between speckle contrast and surface roughness according to an example embodiment.

For monochromatic speckle contrast, a typical curve depicting sensitivity of speckle contrast C to surface roughness $R_q$ is depicted in FIG. 5. The optimal operating range corresponds to a range of speckle contrast with acceptable sensitivity to surface roughness (moderate slope). The horizontal axis is $R_q/\lambda$ ($R_q$ is RMS roughness), suggesting that the operating range is dependent on the wavelength of the monochromatic speckle field. In practice, a sensitivity curve (look up table) of C vs. $R_q$ and corresponding operating range for each $\lambda_i$ could be predetermined during calibration of the system.

In another example, $A_1(x, y), A_2(x, y), \ldots, A_m(x, y)$ can be combined in multiple ways to form multiple new speckle fields. For example, a new (virtual) speckle field $A(x, y)$ can be obtained by combining K monochromatic speckle fields $A_{i_1}(x, y), A_{i_2}(x, y), \ldots, A_{i_K}(x, y)$ where $2 \leq K \leq m$ and $\{i_1, i_2, \ldots, i_K\} \subseteq \{1, 2, \ldots, m\}$:

$$A(x, y) = \sum_{k=1}^{K} A_{i_k} \qquad (3)$$

More specifically, a different combination of wavelengths may produce a different coherence length, giving a polychromatic speckle contrast that may be used to estimate surface roughness of a comparable order of magnitude to the coherence length. In this regard, the coherence length of a polychromatic (spatially) coherent light source is the distance from the light source for which the emitted light remains coherent. If there are enough combinations of coherence lengths, surface roughness of different regimes can be estimated by forming the appropriate speckle field during analysis in post-capture, without prior knowledge of the roughness regime during capture.

Thus, in this example, the analysis includes combining multiple monochromatic speckle fields to form multiple new speckle fields, each new speckle field having a respectively different coherence length, deriving a polychromatic speckle contrast from each of the new speckle fields, and estimating surface roughness of the illuminated material by using the polychromatic speckle contrasts corresponding to coherent lengths that are commensurate with the surface roughness.

Figure 6:
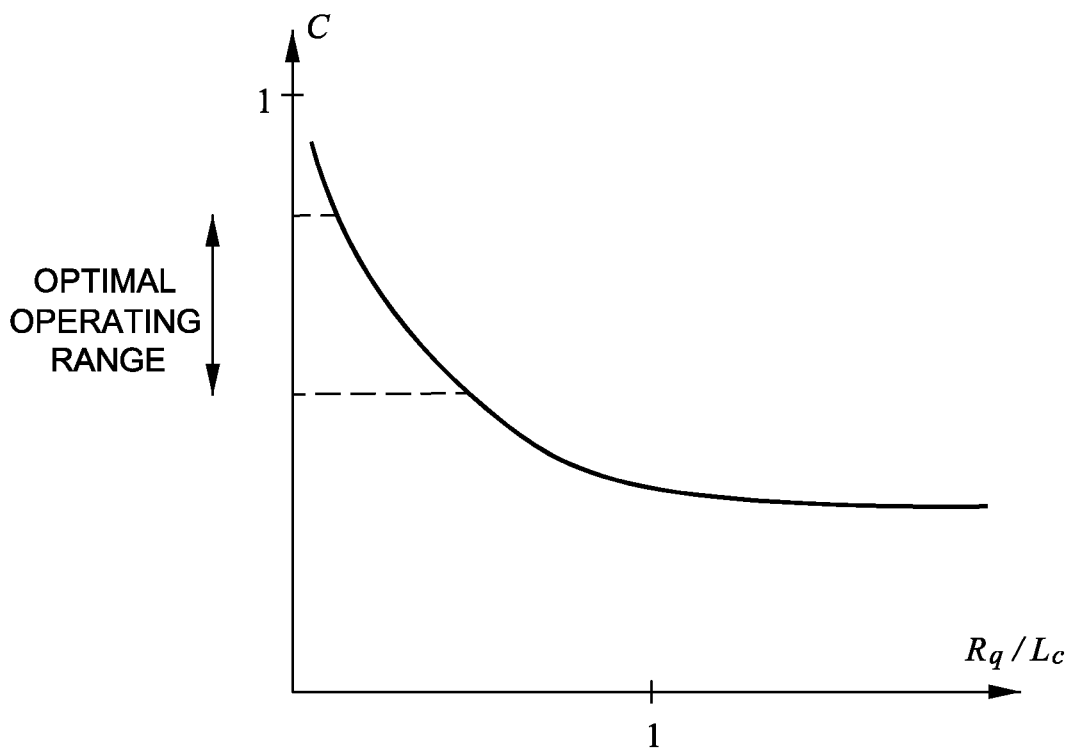
FIG. 6 is a view for explaining a relationship between speckle contrast and surface roughness according to another example embodiment.

For polychromatic speckle contrasts resulting from different combinations of the monochromatic speckle fields, a typical curve depicting sensitivity of polychromatic speckle contrast to surface roughness is depicted in FIG. 6. The optimal operating range corresponds to a range of speckle contrast with acceptable sensitivity to surface roughness (moderate slope) and also away from the limiting case of zero roughness or infinite coherent length. The horizontal axis is $R_q/L_c$ ($L_c$ is coherence length), suggesting that the operating range is dependent on the coherence length of the polychromatic combination.

In that regard, the coherence length for two different but close wavelengths $\lambda$ and $\lambda+\Delta\lambda$ is given by:

$$L_c = \lambda^2/\Delta\lambda \qquad (4)$$

Thus, for example, if two monochromatic speckle fields have wavelengths 657 nm and 670 nm, then individually, the monochromatic speckle contrast might only be able to assess surface roughness in the sub-micron range. However, the combined polychromatic speckle field has a coherence length of about 35 micron. As a result, the polychromatic speckle contrast is able to assess much rougher surfaces. Similar to the monochromatic case, in practice, a sensitivity curve (look up table) of C vs. $R_q$ (not C vs. $R_q/L_c$, i.e., there is no need to determine the coherence length $L_c$ explicitly) and corresponding operating range for each polychromatic speckle field could be predetermined during calibration of the system.

In still another analysis example, $A_1(x, y), A_2(x, y), \ldots, A_m(x, y)$ can be used to compute an m×m correlation matrix, and the correlation matrix can then be used to estimate surface roughness. In that regard, the (i, j)th entry of the correlation matrix may be defined as $<A_i(x, y) A_j(x, y)>$ where $< >$ denotes taking a spatial average. By forming the full m×m correlation matrix, the whole surface roughness regime may ordinarily be covered. Thus, in this example, the analysis includes computing a correlation matrix from the monochromatic speckle fields, where dimensionality of the correlation matrix is based on the number of wavelengths, and estimating surface roughness of the illuminated material from the correlation matrix.

In yet another example, the speckle fields $A_1(x, y), A_2(x, y), \ldots, A_m(x, y)$ can be used to compute feature vectors. Specifically, from each monochromatic speckle field $A_i(x, y)$, statistics can be calculated, such as speckle contrast. By pooling all speckle statistics from $A_1(x, y), A_2(x, y), \ldots, A_m(x, y)$, a feature vector can be obtained that is not only dependent on surface microstructure, but also dependent on wavelength. Consequently, such a feature vector is ordinarily more powerful in material discrimination. Thus, in this example, the analysis includes calculating one or more speckle statistics from each of the monochromatic speckle fields, deriving a feature vector by pooling all of the calculated speckle statistics, and determining a property of the illuminated material from the feature vector.

Accordingly, in some examples, a feature vector is formed based on the analysis of statistical properties of the speckle field images in the stack of speckle field images, and the feature vector is compared to a database of such feature vectors, which may be stored in a memory such as memory 107. Each entry in the database comprises a feature vector matched to an identification of a material from which the feature vector is derived. An identity of the illuminated material is derived based on the comparison.

FIG. 4B is another flow diagram for explaining processing in the device shown in FIGS. 1A to 1C according to an example embodiment. Such processing can be included in step 405, for example. In particular, FIG. 4B shows an example process for determining surface roughness, which may be performed without prior knowledge of the roughness regime. The surface roughness may then be used to determine properties of a material by matching the surface roughness to entries in a database stored in, for example, memory 107.

In step 451, a first monochromatic speckle field and sensitivity look-up table (LUT) is accessed, for example from a database in memory 107. In practice, a LUT of monochromatic speckle contrast/surface roughness and corresponding operating range for each wavelength could be predetermined during calibration of the system. A graph representing an example LUT of monochromatic speckle contrast/surface roughness is shown in FIG. 5.

In step 452, the monochromatic speckle contrast is calculated. The process then proceeds to step 454.

In step 454, there is a determination of whether the calculated monochromatic speckle contrast is within the operating range of the LUT. For example, there may be a determination of whether the calculated monochromatic speckle contrast falls within an optimal operating range. If the calculated monochromatic speckle contrast is within the operating range of the LUT, then the process proceeds to step 459 to determine the surface roughness from the LUT (and perform any end processes, such as outputting the material property determination or material identity derivation via output system 109).

Meanwhile, if the calculated monochromatic speckle contrast is not within the operating range of the LUT, the process proceeds to step 455, where there is a determination of whether there is another monochromatic speckle field that has not been examined. Thus, if there is another monochromatic speckle field, the process proceeds to step 453 to access the next monochromatic speckle field, along with the corresponding sensitivity look-up table (LUT), and the process proceeds to step 452 to calculate the speckle contrast and step 454 to check the operating range of the LUT. On the other hand, if there is not another monochromatic speckle field to be examined (e.g., all monochromatic speckle fields have already been examined), the process proceeds to step 456.

In step 456, a first polychromatic speckle field and sensitivity look-up table (LUT) is accessed, for example from a database in memory 107. A graph representing an example LUT of polychromatic speckle contrast/surface roughness is shown in FIG. 6.

In step 457, the polychromatic speckle contrast is calculated, for example as described above. The process then proceeds to step 460.

In step 460, there is a determination of whether the calculated polychromatic speckle contrast is within the operating range of the LUT. For example, there may be a determination of whether the calculated polychromatic speckle contrast falls within an optimal operating range. If the calculated polychromatic speckle contrast is within the operating range of the LUT, then the process proceeds to step 459 to determine the surface roughness from the LUT (and perform any end processes, such as outputting the material property determination or material identity derivation via output system 109).

On the other hand, if the calculated polychromatic speckle contrast is not within the operating range of the LUT, the process proceeds to step 461, where there is a determination of whether there is another polychromatic speckle field that has not been examined. If there is another polychromatic speckle field, the process proceeds to step 458 to access the next polychromatic speckle field, along with the corresponding sensitivity look-up table (LUT), and the process proceeds to step 457 to calculate the speckle contrast and step 460 to check the operating range of the LUT. On the other hand, if there is not another polychromatic speckle field to be examined (e.g., all polychromatic speckle fields have already been examined), the process proceeds to step 462, where it is determined that the roughness of the material is outside the roughness range that the system can estimate.

By analyzing statistical properties of speckle field images in a stack of speckle field images, it is ordinarily possible to estimate surface roughness without prior knowledge of the range of surface roughness of the materials being measured.

<Other Embodiments>

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method for determining a property of a material, the method comprising:
    illuminating the material with a light beam of controlled spectral and coherence properties, wherein the light beam of controlled spectral and coherence properties originates from a collection of one or more light sources which illuminates the material with multiple wavelengths;
    recording a stack of speckle field images from speckle fields reflected from the illuminated material in multiple spectral channels, wherein the stack of speckle field images comprises multiple speckle field images each being recorded in a respectively different spectral channel;
    analyzing statistical properties of the speckle field images in the stack of speckle field images to determine at least one property of the illuminated material, wherein the analysis comprises:
    estimating a monochromatic speckle field for each of the multiple wavelengths from the stack of speckle field images;
    adding multiple monochromatic speckle fields to form multiple new speckle fields, each new speckle field having a respectively different coherence length;
    deriving a polychromatic speckle contrast value for each of the new speckle fields; and
    estimating a root-mean square (RMS) surface roughness value of the illuminated material by using the polychromatic speckle contrast values corresponding to coherent lengths that are commensurate with the surface roughness.

2. The method according to claim 1, further comprising:
    forming a feature vector based on the analysis of statistical properties of the speckle field images in the stack of speckle field images;
    comparing the feature vector to a database of such feature vectors, wherein each entry in the database comprises a feature vector matched to an identification of a material from which the feature vector is derived; and
    deriving an identity of the illuminated material based on the comparison.

3. The method according to claim 1, wherein the one or more light sources are applied simultaneously.

4. The method according to claim 1, wherein the one or more light sources are applied sequentially.

5. The method according to claim 1, wherein estimating the monochromatic speckle field for each of the multiple wavelengths comprises solving a linear inverse problem whose coefficient matrix is based on spectral sensitivities of the multiple spectral channels.

6. The method according to claim 5, wherein there are at least as many spectral channels as wavelengths, and wherein the monochromatic speckle fields are estimated using a pseudoinverse of the coefficient matrix of the linear inverse problem.

7. The method according to claim 5, wherein there are fewer spectral channels than wavelengths, and wherein the monochromatic speckle fields are estimated by solving an underdetermined linear inverse problem with additional regularizing constraints based on prior statistics for speckle fields.

8. The method according to claim 1, wherein the analysis of statistical properties of the speckle field images in the stack of speckle field images further includes computation of a monochromatic speckle contrast value for each monochromatic speckle field.

9. The method according to claim 1, wherein the analysis of statistical properties of the speckle field images in the stack of speckle field images comprises:
    computing a correlation matrix from the monochromatic speckle fields, wherein dimensionality of the correlation matrix is based on the number of wavelengths and each entry of the correlation matrix is a spatial average of the product of two monochromatic speckle fields; and
    estimating a root-mean square (RMS) surface roughness value of the illuminated material from the correlation matrix.

10. The method according to claim 1, wherein the analysis of statistical properties of the speckle field images in the stack of speckle field images comprises:
    calculating one or more speckle statistics from each of the monochromatic speckle fields;
    deriving a feature vector by pooling all of the calculated speckle statistics; and
    determining a property of the illuminated material from the feature vector.

11. The method according to claim 10, wherein at least one of the calculated speckle statistics includes a speckle contrast value.

12. An apparatus comprising:
    a stage for holding a material;
    a light source positioned to illuminate the material with a light beam of controlled spectral and coherence properties, wherein the light beam of controlled spectral and coherence properties originates from a collection of one or more light sources which illuminates the material with multiple wavelengths;
    a multispectral image sensor positioned at an observation point to record speckle patterns reflected from the illuminated material in each of multiple spectral channels; and
    a computation unit configured to record a stack of speckle field images from speckle fields reflected from the illuminated material, wherein the stack of speckle field images comprises multiple speckle field images each being recorded in a respectively different spectral channel, and configured to analyze statistical properties of the speckle field images in the stack of speckle field images to determine at least one property of the illuminated material,
    wherein the analysis comprises:
    estimating a monochromatic speckle field for each of the multiple wavelengths from the stack of speckle field images;
    adding multiple monochromatic speckle fields to form multiple new speckle fields, each new speckle field having a respectively different coherence length;
    deriving a polychromatic speckle contrast value for each of the new speckle fields; and
    estimating a root mean-square (RMS) surface roughness value of the illuminated material by using the polychromatic speckle contrast values corresponding to coherent lengths that are commensurate with the surface roughness.

13. The apparatus according to claim 12, wherein the computation unit is further configured to:
    form a feature vector based on the analysis of statistical properties of the speckle field images in the stack of speckle field images;
    compare the feature vector to a database of such feature vectors, wherein each entry in the database comprises a feature vector matched to an identification of a material from which the feature vector is derived; and
    derive an identity of the illuminated material based on the comparison.

14. The apparatus according to claim 12, wherein the computation unit is configured such that the analysis of statistical properties of the speckle field images in the stack of speckle field images comprises:
    computing a correlation matrix from the monochromatic speckle fields, wherein dimensionality of the correlation matrix is based on the number of wavelengths and each entry of the correlation matrix is a spatial average of the product of two monochromatic speckle fields; and
    estimating a root-mean square (RMS) surface roughness value of the illuminated material from the correlation matrix.

15. The apparatus according to claim 12, wherein the computation unit is configured such that the analysis of statistical properties of the speckle field images in the stack of speckle field images comprises:
    calculating one or more speckle statistics from each of the monochromatic speckle fields;
    deriving a feature vector by pooling all of the calculated speckle statistics; and
    determining a property of the illuminated material from the feature vector.

* * * * *